ns Patent

Argoudelis et al.

[11] 4,001,267
[45] Jan. 4, 1977

[54] FELDAMYCIC ACID
[75] Inventors: Alexander D. Argoudelis, Portage; Lubomir Baczynskyj; Stephen A. Mizsak, both of Kalamazoo, all of Mich.
[73] Assignee: The Upjohn Company, Kalamazoo, Mich.
[22] Filed: Sept. 22, 1975
[21] Appl. No.: 615,769
[52] U.S. Cl. .......................... 260/309; 260/112.5 R
[51] Int. Cl.² ..................................... C07D 233/64
[58] Field of Search .................................. 260/309
[56] References Cited
OTHER PUBLICATIONS
Greenstein et al., I, Chemistry of the Amino Acids, vol. 2, pp. 1366–1371, N. Y., Wiley, 1961.
Greenstein et al., II, Chemistry of the Amino Acids, vol. 2, p. 771, N. Y., Wiley, 1961.
Recsei et al., Chem. Abst., 1970, vol. 72, No. 128955u.

Primary Examiner—Natalie Trousof
Attorney, Agent, or Firm—Roman Saliwanchik

[57] ABSTRACT

Feldamycic acid, having the structure

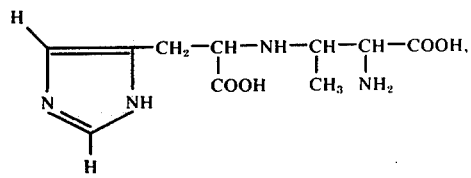

is obtained by the hydrolysis of the antibiotic feldamycin (U-48,266) and can be coupled with nutritional amino acids to give peptides, useful as nutritional supplements.

5 Claims, No Drawings

FELDAMYCIC ACID

BACKGROUND OF THE INVENTION

Feldamycic acid is obtained by hydrolysis of the antibiotic feldamycin (U-48,266). Antibiotic U-48,266 is disclosed in pending U.S. patent application Ser. No. 556,573, filed on Mar. 10, 1975.

BRIEF SUMMARY OF THE INVENTION

Feldamycic acid can be prepared by acid or base hydrolysis of feldamycin. Acid hydrolysis is preferred. Hydrolysis of feldamycin yields feldamycic acid and the known amino acid N-methylhistidine.

Feldamycic acid can be coupled with nutritional amino acids, for example, glycine, alanine, valine, leucine, isolecine, phenylalanine, tyrosine, proline, hydroxyproline, serine, threonine, cysteine, cystine, methionine, tryptohan, aspartic acid, glutamic acid, arginine, lysine and histidine to give peptides useful as nutritional supplements for animals and microorganisms.

DETAILED DESCRIPTION

Feldamycic acid can be shown by the following structure:

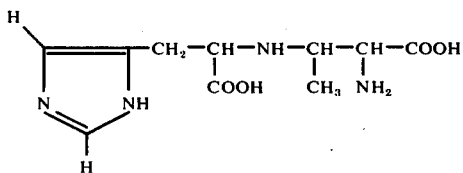

Feldamycic acid can be prepared by acid hydrolysis of feldamycin. The hydrolysis can be conducted with a mineral acid ranging from 2 to 8 N. Examples of acids which can be used are hydrochloric, sulfuric and phosphoric. The reaction can be conducted at a temperature of 0° to reflux. Reflux is preferred since lower temperatures prolong the completion of the reaction. Feldamycic acid can be recovered from the reaction mixture by first concentrating said mixture to dryness and then subjecting the dry material to chromatography over silica gel using 95% ethanol-water mixtures as a solvent system to separate feldamycic acid from N-methylhistidine.

Feldamycic acid also can be isolated from the hydrolysate by chromatography over either anionic or cationic exchange resins, for examples, Dowex-1, Dowex-2, Dowex-50, IR-45 and IRC-50. The Dowex resins are supplied by the Dow Chemical Company, Midland, Michigan, and the IR and IRC resins are supplied by Rohn and Haas Company, Philadelphia, Pennsylvania.

Feldamycic acid and N-methylhistidine also can be separated by partition techniques, for example, distribution, batch-wise or countercurrently, between 1-butanol-water (1:1). and like solvent systems. Partition chromatography can be used for the separation of the two amino acids using diatomaceous earth as the support and solvent systems consisting of the upper phase of systems resulting by mixing water and a water-immiscible solvent such as higher alcohols, ketones or esters.

Since feldamycic acid is an amphoteric substance, it can form salts with both acids and bases. Examples of inorganic and organic acids which can be used to form salts with feldamycic acid, but which examples should not be considered limiting, are hydrochloric, sulfuric, phosphoric, acetic, succinic, citric, lactic, maleic, fumaric,, pamoic, cholic, palmitic, mucic, camphoric, glutaric, glycolic, phthalic, tartaric, lauric, stearic, salicylic, 3-phenylsalicylic, 5-phenylsalicylic, 3-methylglutaric, orthosulfobenzoic, cyclohexanesulfamic, cyclopentanepropionic, 1,2-cyclohexanedicarboxylic, 4-cyclohexenecarboxylic, octadecenylsuccinic, octenylsuccinic, methanesulfonic, benzenesulfonic, helianthic, Reinecke's, dimethyldithiocarbamic, sorbic, monochloroacetic, undecylenic, 4'-hydroxyazobenzene-4-sulfonic, octadecylsulfuric, picric, benzoic, cinnamic, and like acids.

Salts of feldamycic acid can be formed with inorganic or organic bases. Such salts can be prepared, as for example, by dissolving feldamycic acid in water, adding a dilute base until the pH of the solution is about 10.0 to 11.0, and freeze-drying the solution to provide a dried residue consisting of the salt. Feldamycic acid salts with inorganic cations which can be formed include the sodium, potassium, and calcium salts. Other salts of feldamycic acid, including those with organic bases such as primary, secondary, and tertiary monoamines as well as with polyamines, also can be formed using the above-described or other commonly employed procedures. Other valuable salts are obtained with therapeutically effective bases which impart additional therapeutic effects thereto. Such bases are, for example, the purine bases such as theophylline, theobromine, caffeine, or derivatives of such purine bases; antihistaminic bases which are capable of forming salts with weak acids; pyridine compounds such as nicotinic acid amide, isonicotinic acid hydrazide, and the like; phenylalkylamines such as adrenaline, ephedrine, and the like; chlorine, and others. Salts of feldamycic acid can be used for the same purposes as the parent compound.

Feldamycic acid can be coupled with nitritional amino acids, for example, glycine, alanine, valine, leucine, isoleucine, phenylalanine, tyrosine, proline, hydroxyproline serine, threonine, cysteine, cystine, methionine, tryptophan, aspartic acid, glutamic acid, arginine, lysine and histidine to give peptides useful as nutritional supplements for animals and microorganisms as disclosed in U.S. Pat. No. 3,256,095.

Peptide formation reactions are well known. See "The Peptides" by Eberhard Schröder and Klaus Lübke, Volume 1, Methods of Peptide Synthesis, Academic Press, New York, 1965.

The following examples are illustrative of the process and products of the invention, but are not to be construed as limiting. All percentages are by weight and all solvent mixture proportions are by volume unless otherwise noted.

EXAMPLE 1

Two grams of feldamycin is dissolved in 100 ml of 6 N aqueous hydrochloric acid. The solution is kept at reflux for 16 hours. The hydrolysate is then concentrated to dryness to give a mixture of N-methylhistidine hydrochloride and feldamycic acid hydrochloride.

EXAMPLE 2

The preparation, as described in Example 1, is dissolved in water and passed over a chromatography column containing Dowex-1 ($Cl^-$). The column is washed with water and then eluted gradiently using 0.05. to 0.1 N aqueous hydrochloric acid. N-methylhistidine hydrochloride is eluted first followed by feldamycic acid hydrochloride.

EXAMPLE 3

A silica gel chromatography column is prepared from silica gel (Merck, Darmstadt) packed in 95% ethanol-water (70:30 v/v). A hydrolysate, prepared as described in Example 1, is dissolved in the solvent and added on top of the column. The column is eluted using the same solvent system. Fractions are analyzed by thin layer chromatography (tlc) using Eastman's silica gel 6061; 95% ethanol-water 70:30; and development with ninhydrin reagent. Fractions containing feldamycic acid are indicated by their strong reaction with ninhydrin. These fractions are concentrated to dryness to give relatively pure feldamycic acid.

EXAMPLE 4

Feldamycin is hydrolyzed by refluxing with 2 N aqueous sodium hydroxide for 24 hours. A similar hydrolysis can be conducted by substituting saturated barium hydroxide as the base. The resulting reaction mixture contains the sodium salts of feldamycic acid and N-methylhistidine. This mixture is titrated with 1 N HCl to a pH of about 6.0 to 6.5 and then subjected to chromatographic procedures as disclosed in the prior examples, to yield N-methylhistidine preparations and feldamycic acid preparations.

We claim:

1. Feldamycic acid, a compound having the following structure:

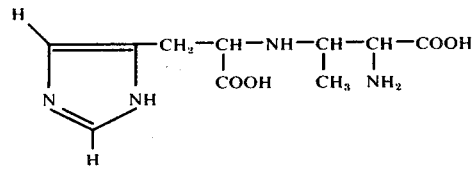

and acid and base addition salts thereof.

2. Feldamycic acid hydrochloride, a compound according to claim 1.

3. A process for preparing feldamycic acid which comprises hydrolyzing feldamycin with a strong mineral acid to a hydrolysate containing N-methylhistidine and feldamycic acid, and recovering feldamycic acid from said hydrolysate.

4. A process, according to claim 3, wherein the strong mineral acid is 6 N aqueous hydrochloric acid.

5. A process, according to claim 3, for recovering feldamycic acid from a hydrolysate containing N-methylhistidine hydrochloride and feldamycic acid hydrochloride which comprises subjecting said hydrolysate to chromatographic procedures.

* * * * *